United States Patent [19]

Smith

[11] 4,243,037
[45] Jan. 6, 1981

[54] FECAL IMPACTION REMOVER

[76] Inventor: Norma J. Smith, 1001 King St., Plaquemine, La. 70764

[21] Appl. No.: 54,285

[22] Filed: Jul. 2, 1979

[51] Int. Cl.³ .............................................. A61B 17/00
[52] U.S. Cl. ................................ 128/303 R; 128/240
[58] Field of Search ........... 128/1 R, 303 R, 341–345, 128/240–241

[56] References Cited

U.S. PATENT DOCUMENTS

| 3,022,787 | 2/1962 | Daniel | 128/345 X |
| 3,316,912 | 5/1967 | Whitaker | 128/303R |

FOREIGN PATENT DOCUMENTS 439133  11/1935  United Kingdom ..................... 128/343

Primary Examiner—Dalton L. Truluck
Attorney, Agent, or Firm—Roy, Kiesel, Patterson & McKay

[57] ABSTRACT

A device for breaking up impacted fecal from the rectum comprising an outer hollow tube having an opening at one end for introducing an enema solution into the tube cavity and having an opening at the other end for allowing the enema solution to pass from the tube cavity into the rectum, and a plunger assembly shaped to slidingly fit in the tube cavity and having prongs attached at one end which can be used to digitally break up the impacted fecal.

3 Claims, 3 Drawing Figures

FECAL IMPACTION REMOVER

BACKGROUND OF THE INVENTION

1. Field of the Invention

This invention relates broadly to medical devices and, more particularly, to a device for breaking up impacted fecal from the rectum of a person.

2. Prior Art

One unpleasant problem faced today in hospitals and nursing homes is the treatment of patients having impacted fecal. In many cases, the fecal has become so impacted that normal treatment by enemas is not successful. In these cases, the doctor or registered nurse must physically insert their fingers into the rectum of the patient and attempt to break up the hardened stool. Not only is this a traumatic experience to the patient, but can result in a tearing of the rectum wall by the fingernail of the doctor or registered nurse.

For the above reasons, a device which can remove impacted fecal quickly and without harm to the patient is sorely needed by hospitals, nursing homes and other similar institutions.

SUMMARY OF THE INVENTION

Therefore, one object of this invention is to provide a device which can quickly, but safely remove impacted fecal from the rectum of a person.

This and other objects and advantages of this invention shall become apparent from the ensuing descriptions of the invention.

Accordingly, a device for breaking up impacted fecal in a rectum is provided comprising an outer hollow tube having a cavity into which is located a plunger assembly having a shape which provides a passageway between the wall of the tube and the plunger assembly, wherein the tube has a means located at the top end of the tube for introducing an enema solution into the passageway and openings located at the bottom section of the tube to allow the enema solution to flow out of the passageway and into the rectum, and wherein the plunger assembly has prong means attached at one end of the plunger assembly rod to break up the impacted fecal.

PREFERRED EMBODIMENTS OF THE INVENTION

Figure 2:
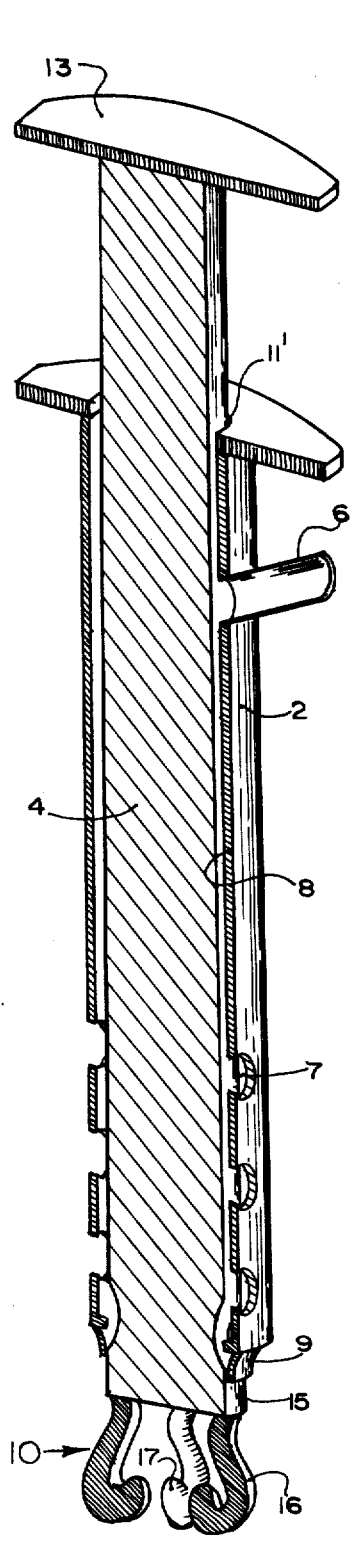
FIG. 2 is a cross-sectional view taken along lines 2—2 of FIG. 1.
Figure 1:
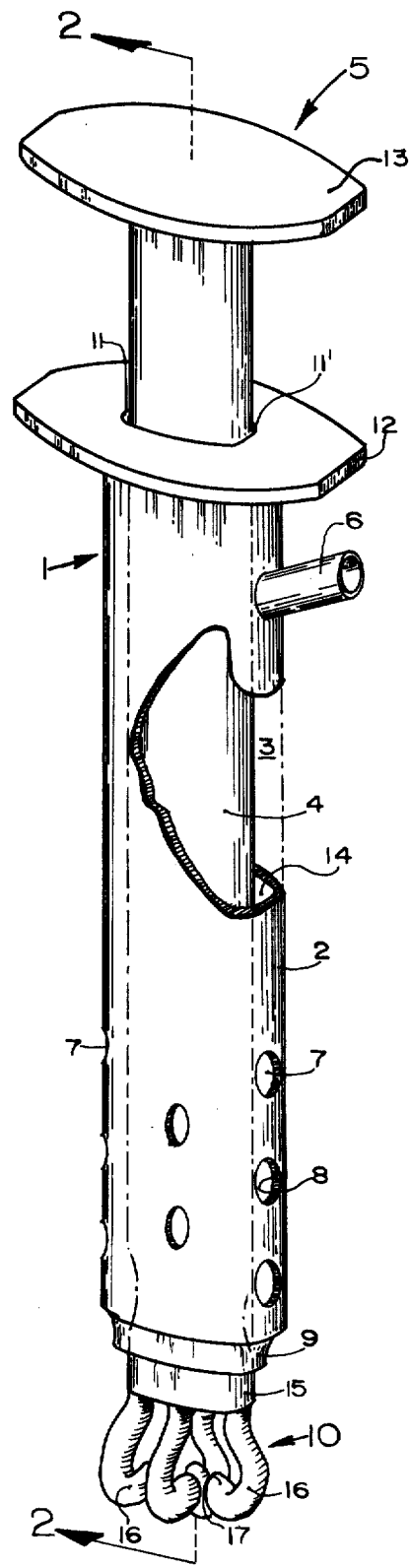
FIG. 1 is a three dimensional cutaway view of one embodiment of the invention.

Referring to FIGS. 1 and 2, the impacted fecal removal device, denoted generally by the numeral 1, is shown having an outer tube 2 having a cavity 3 into which fits rod 4 of plunger assembly 5.

Tube 2 is provided with a hollow stem piece 6 or similar means for connection to a source of enema solution. Stem piece 6 is preferably located at the upper end of tube 2 while openings 7 extending through tube wall 8 are located in the lower section of tube 2. In a preferred embodiment, openings 7 are spaced about the circumference of tube 2 to allow the enema solution to enter all areas of the rectum as discussed below. In another preferred embodiment, tube 2 is provided with a plunger guide lip section 9 that has an opening shaped similarly to that of rod 4 to control the direction which prong means 10 are inserted into the rectum. More preferably, a second guide structure 11 is also provided at the opposite end of tube 2 having an opening 11' also similarly shaped to that of rod 4. In another preferred embodiment, a finger gripping shoulder section 12 extends outward from tube 2 to provide means for the operator to insert the tube in the rectum and to steady tube 2 during the manipulation of plunger assembly 5.

Plunger assembly 5 preferably also comprises a finger gripping shoulder section 13 attached to one end of rod 4 for better control during the manipulation of plunger assembly 5. In a preferred embodiment, rod 4 has a diameter less than that of cavity 3 so that a passageway 14 is formed between tube wall 8 and rod 4 to allow the enema solution to flow from stem piece 6 down passageway 14 to openings 7.

In a preferred embodiment, prong means 10 will comprise multiple prongs 16 extending down from the bottom end 15 of rod 4. More preferably, each prong 16 will be curved so that its end 17 is directed away from the adjacent portion of the rectum wall as shown. Furthermore, it is preferable that each prong 16 not be shaped to have sharp cutting surfaces and that it also be constructed so that each prong has some flexibility.

Figure 3:
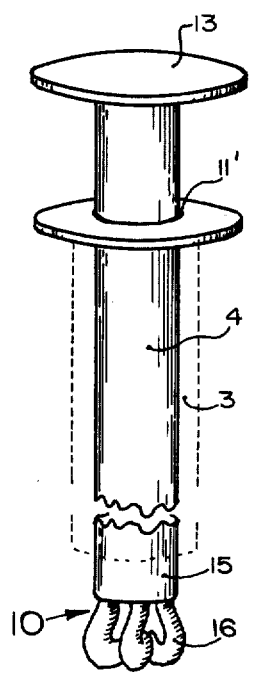
FIG. 3 is a three dimensional view of a preferred embodiment of the plunger assembly utilized in this invention.

Referring now to FIG. 3, a preferred shape of rod 4 is illustrated. The circular cross-section allows rod 4 to be rotated as well as vertically moved.

In operation, tube 2 is inserted in the patient's rectum, preferably a distance so that prongs 16 contact the impacted fecal. Enema solution then enters stem piece 6 and flows down passageway 14 and out openings 7 into the rectum where it lubricates the rectum. The doctor or registered nurse then rotates and moves rod 4 up and down so that prongs 16 strike and break up the impacted fecal. If desired, part of the broken fecal pieces can be brought up tube 2 and removed. Once the impacted fecal has been sufficiently broken up, tube 2 is removed and the patient can then pass the fecal by normal body functions.

There are, of course, other modifications and features not specifically illustrated and described but which are meant to be included within the scope of the invention as defined by the following claims.

What I claim is:

1. A device for breaking up impacted fecal in a rectum comprising an outer hollow tube having a cavity extending therethrough into which is located a plunger assembly having a rod means slidingly extending through said cavity and shaped to form a passageway between said tube and said rod, said plunger assembly having prong means attached at one end of said rod to break up said impacted fecal, said tube comprises a connecting means located at one end of said tube opposite prong means for receiving an enema solution, said connecting means having a channel connecting to said passageway to allow said enema solution to flow into said passageway and wherein said tube comprises openings connected to said passageway and located at another end section opposite said connecting means allowing said enema solution to flow from said passageway to said rectum.

2. A device according to claim 1 wherein said openings are spaced about the circumference of said tube.

3. A device according to claim 1 wherein said tube comprises a plunger guide lip section attached at the lower end of said tube adjacent said prong means, said lip section having an opening shaped similarly to that of the cross-section of said rod, but of sufficient size to allow said rod to slidingly pass through said lip section opening, said tube comprising a second guide lip section attached to the opposite end of said tube, said second lip section having a second lip section opening having a cross-section similar to that of the cross-section of said rod, but of sufficient size to allow said rod to slidingly pass through said second lip section opening.

* * * * *